(12) United States Patent
Leng et al.

(10) Patent No.: US 9,754,387 B2
(45) Date of Patent: Sep. 5, 2017

(54) SYSTEM AND METHOD FOR IMPROVED ENERGY SERIES OF IMAGES USING MULTI-ENERGY CT

(71) Applicant: Mayo Foundation For Medical Education And Research, Rochester, MN (US)

(72) Inventors: Shuai Leng, Rochester, MN (US); Cynthia H. McCollough, Byron, MN (US); Lifeng Yu, Byron, MN (US); Joel G. Fletcher, Oronoco, MN (US); Charles A. Mistretta, Madison, WI (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 14/944,666

(22) Filed: Nov. 18, 2015

(65) Prior Publication Data
US 2016/0086358 A1    Mar. 24, 2016

Related U.S. Application Data

(63) Continuation of application No. 13/809,800, filed as application No. PCT/US2011/044390 on Jul. 18, 2011, now Pat. No. 9,208,585.

(60) Provisional application No. 61/365,191, filed on Jul. 16, 2010.

(51) Int. Cl.
*G06T 11/00* (2006.01)
*A61B 6/03* (2006.01)
*A61B 6/00* (2006.01)
*G01N 23/04* (2006.01)
*G06T 5/20* (2006.01)

(52) U.S. Cl.
CPC ............ *G06T 11/003* (2013.01); *A61B 6/032* (2013.01); *A61B 6/4241* (2013.01); *A61B 6/482* (2013.01); *A61B 6/50* (2013.01); *A61B 6/5205* (2013.01); *G01N 23/046* (2013.01); *G06T 5/20* (2013.01); *G01N 2223/1016* (2013.01); *G01N 2223/419* (2013.01); *G01N 2223/423* (2013.01)

(58) Field of Classification Search
CPC combination set(s) only.
See application file for complete search history.

(56) References Cited

U.S. PATENT DOCUMENTS

2006/0109949 A1* 5/2006 Tkaczyk ................ A61B 6/032 378/4
2008/0226017 A1* 9/2008 Altman .................. A61B 6/482 378/4

\* cited by examiner

*Primary Examiner* — David E Smith
*Assistant Examiner* — Hsien Tsai
(74) *Attorney, Agent, or Firm* — Quarles & Brady LLP (57) ABSTRACT

A method for creating an energy series of images acquired using a multi-energy computed tomography (CT) imaging system having a plurality of energy bins includes acquiring, with the multi-energy CT imaging system, a series of energy data sets, where each energy data set is associated with at least one of the energy bins. The method includes producing a conglomerate image using at least a plurality of the energy data sets and, using the conglomerate image, reconstructing an energy series of images, each image in the energy series of images corresponding to at least one of the energy data sets.

20 Claims, 6 Drawing Sheets

SYSTEM AND METHOD FOR IMPROVED ENERGY SERIES OF IMAGES USING MULTI-ENERGY CT

CROSS-REFERENCE TO RELATED APPLICATIONS

This application is a continuation application of U.S. patent application Ser. No. 13/809,800 filed Jan. 11, 2013, which is a 371 application of PCT/US11/44390 filed Jul. 18, 2011, which claims the benefit of U.S. Provisional Application No. 61/365,191, filed Jul. 16, 2010, all of which are incorporated herein by reference.

BACKGROUND OF THE INVENTION

The present invention relates to computed tomography (CT) imaging and, more particularly, to systems and methods for energy domain data correction in spectral CT imaging to control noise and radiation dose.

In a computed tomography system, an x-ray source projects a fan or cone shaped beam which is collimated to lie within an X-Y plane of a Cartesian coordinate system, termed the "imaging plane." The x-ray beam passes through the object being imaged, such as a medical patient or other non-medical patient or object, such as in industrial CT imaging, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique, however, other image reconstruction processes are also well known. This process converts the attenuation measurements from a scan into integers called "CT numbers" or "Hounsfield units", which are used to control the brightness of a corresponding pixel on a display.

The term "generation" is used in CT to describe successively commercially available types of CT systems utilizing different modes of scanning motion and x-ray detection. More specifically, each generation is characterized by a particular geometry of scanning motion, scanning time, x-ray beam shape, and detector system.

The first generation utilized a single linear x-ray beam ("pencil beam") and a single scintillation crystal-photomultiplier tube detector for each tomographic slice. After a single linear motion or traversal of the x-ray tube and detector, during which time 160 separate x-ray attenuation or detector readings are typically taken, the x-ray tube and detector are rotated through one degree and another linear scan is performed to acquire another view. This is repeated typically to acquire 180 views.

A second generation of CT systems was developed to shorten the scanning times of first generation systems by gathering the attenuation data more quickly. In these units, a modified fan beam, including anywhere from 3-52 individual collimated x-ray beams, and a number of detectors equal to the number of collimated x-ray beams are used. Individual beams resemble the single beam of a first generation scanner; however, a collection of from 3-52 of these beams contiguous to one another allows multiple adjacent regions of tissue to be examined simultaneously. The configuration of these contiguous regions of tissue resembles a fan, with the thickness of the fan material determined by the collimation of the beam and in turn determining the slice thickness. Because of the angular difference of each beam relative to the others, several different angular views through the body slice are being examined simultaneously. Superimposed on this is a linear translation or scan of the x-ray tube and detectors through the body slice. Thus, at the end of a single translational scan, during which time 160 readings may be made by each detector, the total number of readings obtained is equal to the number of detectors times 160. The increment of angular rotation between views can be significantly larger than with a first generation unit, up to as much as 36°. Thus, the number of distinct rotations of the scanning apparatus can be significantly reduced, with a coincidental reduction in scanning time. By gathering more data per translation, fewer translations are needed.

To obtain even faster scanning times it is necessary to eliminate the complex translational-rotational motion of the first two generations. Third generation scanners therefore use a much wider, "divergent" fan beam. In fact, the angle of the beam may be wide enough to encompass most or all of an entire patient section without the need for a linear translation of the x-ray tube and detectors. As in the first two generations, the detectors, now in the form of a large array, are rigidly aligned relative to the x-ray beam, and there are no translational motions at all. The tube and detector array are synchronously rotated about the patient through an angle of 180-360°. Thus, there is only one type of motion, allowing a much faster scanning time to be achieved. After one rotation, a single tomographic section is obtained.

Fourth generation scanners also feature a divergent fan beam similar to the third generation CT system. As before, the x-ray tube rotates through 360° without having to make any translational motion. However, unlike in the other scanners, the detectors are not aligned rigidly relative to the x-ray beam. In this system only the x-ray tube rotates. A large ring of detectors are fixed in an outer circle in the scanning plane. The necessity of rotating only the tube, but not the detectors, allows faster scan time.

Beyond these large "generational" distinctions between CT technology, a number of additional advancements have been made. For example, dual energy and even dual source CT systems have been developed. In either case, x-ray dose of different energy levels are used to acquire two image data sets from which a low energy and a high energy image may be reconstructed. As will be described, a wide variety of information can than be determined from the subject by analyzing the characteristics and variations between the low energy data set and the high energy data set.

In addition, photon counting (PC) and energy discriminating (ED) detector CT systems have the potential to greatly increase the medical benefits of CT. Unlike the above-described "traditional" CT detectors, which integrate the charge generated by x-ray photon interactions in the detector but provide no specific energy information regarding individual photons, PC detectors record the energy deposited by each individual photon interacting with the detector. PC detector system can provide new clinical abilities due to an ability to differentiate materials such as a contrast agent in the blood and calcifications that may otherwise be indistinguishable in traditional CT systems. Also, they can improve the signal to noise ratio (SNR) by reducing electronic and swank noise. PC and ED CT systems generally produce less image noise for the same dose than photon energy integrating detectors and hence can be more dose efficient than conventional CT systems. Also, they can improve SNR by assigning optimal, energy dependent weighting factors to the detected photons and achieve additional SNR improvements by completely or partially rejecting scattered photons. Further still, PC detectors allow measurement of transmitted, energy-resolved spectra from a single exposure at one tube potential.

The development of PC detectors for micro-CT and whole-body CT applications has enabled a new dimension of CT imaging, namely "spectral CT" or "multi-energy CT." These advances have attracted considerable attention in the scientific and research communities, due to the potential for enhanced material characterization utilizing spectral x-ray information. This lays the groundwork for many clinical applications, such as detecting new biomarkers, such as iron in vulnerable plaque, multi-contrast imaging, such as iodine and barium imaging of the bowel luminal wall and intra-lumen contents, and exploring intrinsic tissue contrast, cancerous tissue compared to normal tissue.

In contrast to conventional CT systems, where photons are measured and recorded in a single transmission data set, spectral CT generates multiple data sets, with each data set measuring only those photons with energies between predefined low and high energy thresholds. Because the x-ray attenuation of a material depends on the photon energy, material-specific information is then built into each energy-specific data set. Measured data from each energy bin is then reconstructed independently to generate a series of CT images, each corresponding to a specific energy range. These images are highly correlated, since the anatomic geometry and physical density of the object remains unchanged for any time point. Only the total x-ray attenuation values, that is, CT numbers, differ, according to the material type and selected photon energy bin. An attenuation-energy curve can be generated from these multiple image series, each image corresponding to one energy bin. Since each material has its own attenuation-energy curve, material identification/differentiation can then be achieved using multi-energy CT.

Figure 1:
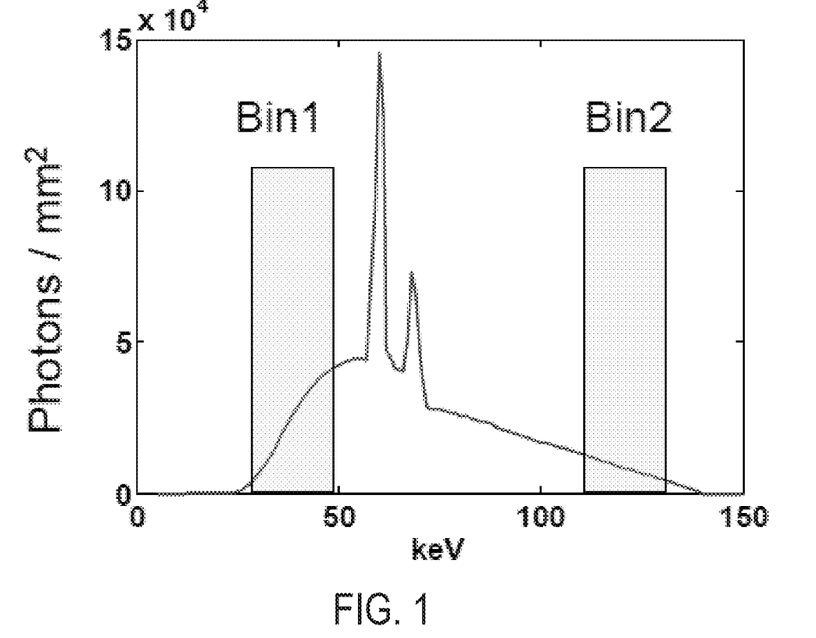
FIG. 1 is a graph illustrating energy with respect to two exemplary bins used with photon counting detectors and relative to a broad brehmsstralung spectrum.

The appropriate selection of energy bins, for example, the number of energy bins and width of each energy bin, has a significant affect on the outcome of spectral imaging. A narrow energy bin has better energy resolution compared to a wider energy bin, and hence enables better material identification/differentiation. For example, FIG. 1 shows a graph of two energy bins used to separate iron, which is a biomarker for vulnerable plaques, from calcium. A narrow energy window width of 20 keV was used and the two energy bins were widely separated in the x-ray spectrum. The dual energy ratio difference, which is an indicator of material separation capability, or the dual-energy "contrast" between two materials, using these energy windows were compared with conventional dual energy CT, in which wider energy windows, with a low of 0 to 80 kVp and an high of 0 to 140 kVp were used. Significant improvement was observed using the narrow beam energy windows (20 keV). However, a significant limitation of using narrow bins is that the number of photons available in each energy bin is much smaller than the total number of photons detected. For the scenario in FIG. 1, only a small portion of total photons were used in each energy-specific image and a large fraction of photons in between energy bin 1 and 2 were discarded.

As image noise is proportional to the inverse square root of available photons, image noise is correspondingly higher using a narrow energy bin than a wide energy bin. Thus, a critical problem occurs. Specifically, in order to identify or differentiate materials using spectral CT, the differences in effective atomic number or signal must be amplified by: 1) using narrow energy bins and 2) separating the energy bins as widely as possible. However, this requirement excludes a large percentage of the detected energy spectrum from the considered image data. Thus, the resultant images, in which dual-energy signal is increased, suffer from increased noise. For narrow energy bins, especially in the lower energy range, the image noise may be so high as to make it impossible to detect small differences in material composition, that is, the signal to noise ratio (SNR) is too low. Further, a large portion of the dose delivered to the patient is wasted, creating a difficult dilemma of the clinician balancing between dose delivered and achieving a desired SNR. Thus, the requirements for increasing dual-energy signal are in direct conflict with the requirements for decreasing image noise in the individual energy images and in any material composition images derived from the energy specific images.

Figure 2:
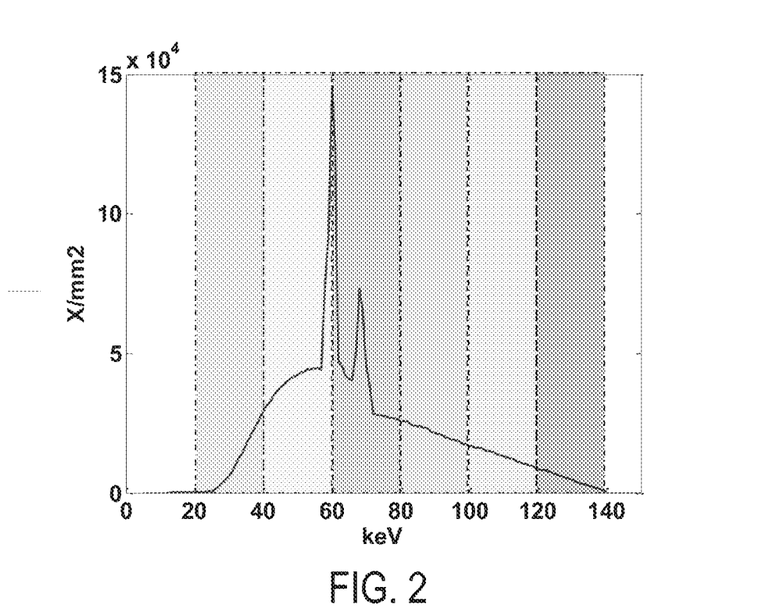
FIG. 2 is a graph illustrating that a dual-energy signal between iron and calcium is maximized with use of the two, widely separated energy bins compared to energy windows currently used with integrating detector technology (80/140 kV=80 and 140 kVp beams or 80/140Sn=80 kVp and 140 kVp beams, where the 140 kVp beam has been filtered with approximately 0.4 mm of tin (Sn)) to selectively reduce the number of photons below 80 keV, which increases the dual-energy signal due to the increased separation of mean beam energy.

Similar observations exist for the selection of total number of energy bins. For a given x-ray spectrum, a given kVp, more energy bins provide more measurements of energy dependent information. With multiple data points available along the attenuation-energy curve, better curve-fitting, consequently better material differentiation is achieved. However, more bins also dictates narrower widths for each bin and hence fewer photons in each bin. Turning to FIG. 2, a scenario in which 6 energy bins were used is illustrated. In FIG. 2, 6 separate measurements in the energy domain corresponding to the 6 energy bins are available. However, the number of photons in each energy bin is only ⅙ of the total photons delivered. Accordingly, the noise in each image is then significantly high.

Therefore, an intrinsic tradeoff exists in the selection of energy bins (number, width, and placement) for spectral CT, resulting in the described tradeoff between energy-specific signal (material identification/differentiation information) and noise. This tradeoff limits the clinical applications of spectral CT. For example, for the differentiation between iron (a biomarker for plaque vulnerability) from calcium in vascular plaques, narrow energy bins are generally used due to the very small concentration iron amidst a typically higher concentration of calcium (i.e. there is a very weak signal). Due to the small signal size, image noise must be strictly controlled to allow the detection of iron, and hence the identification of those plaques more likely to rupture and cause acute myocardial infarction. Thus, a dilemma is presented of increasing signal size through appropriate selection of the energy bins is counterproductive due to the increase in image noise. Although increased photons (dose) could potentially be used, increases in patient dose above existing levels will prevent clinical application due to the heightened concern about ionizing radiation in medicine and potential long-term effects of such radiation on patients. An increased dose will also likely require higher power and cooling requirements on the x-ray tube and generator, as current coronary CT angiography already uses the upper limits of tube/generator technology. Addressing this with use of longer scan times, such as using longer gantry rotation times, would sacrifice image quality with motion artifact and hence blur out the small signal that is sought.

Accordingly, it would be desirable to have a system and method for creating an energy series of images with reduced noise and increased signal to noise ratio.

SUMMARY OF THE INVENTION

The present invention overcomes the aforementioned drawbacks by providing a system and method for creating an energy series of images acquired using a multi-energy computed tomography (CT) imaging system having a plurality of energy bins. Using the multi-energy CT imaging system, a series of energy data sets is acquired, where each energy data set is associated with at least one of the energy bins. A conglomerate image is produced using a plurality of the energy data sets and, using the conglomerate image, an energy series of images is reconstructed, where each image in the energy series of images corresponds to at least one of the energy data sets. Thus, the present invention seeks to exploit a correlation of information in the energy domain to reduce image noise in each energy-specific image, not just in a processed material-composition image. As such, the present invention improves material differentiation in spectral CT by allowing selection of desired energy bins and, in particular, the number of bins, the width of the bins, and the location of the bins, without paying a noise penalty.

In accordance with one aspect of the invention, a method for creating an energy series of images acquired using a computed tomography (CT) imaging system is disclosed that includes acquiring a series of energy-selective data sets, each energy-selective data set associated with energy bin and producing a conglomerate data set from the energy-selective data sets including data associated with at least a plurality of the energy bins. The method also includes weighting each of the energy-selective data sets using the conglomerate data set and reconstructing an enhanced energy series of images, where each image in the enhanced energy series of images corresponds to at least one of the energy data sets.

In accordance with another aspect of the invention, a method for creating an energy series of images acquired using a multi-energy computed tomography (CT) imaging system having a plurality of energy bins is disclosed that includes acquiring a series of energy data sets, each energy data set associated with at least one of the energy bins. The method also includes producing a conglomerate data set using at least a plurality of the energy data sets and using the conglomerate data set, generating at least one of an enhanced material-specific image and an enhanced energy series of images, each image corresponding to at least one of the energy data sets.

In accordance with still another aspect of the invention, a computed tomography (CT) imaging system is disclosed that includes an x-ray source configured to emit x-rays toward an object to be imaged, a detector configured to receive x-rays that are attenuated by the object, and a data acquisition system (DAS) connected to the detector to receive an indication of received x-rays. The system also includes a computer system coupled to the DAS to receive the indication of the received x-rays and programmed to segregate the indication of the received x-rays into a series of energy data sets based on an energy level associated with received x-rays. The computer is further programmed to produce a conglomerate data set using data from at least a plurality of the energy data sets and reconstruct at least one of an enhanced material-specific image and an enhanced energy series of images, each image in the at least one of the enhanced material-specific image and enhanced energy series of images corresponding to at least one of the energy data sets, using the series of energy data sets and the conglomerate data set.

Various other features of the present invention will be made apparent from the following detailed description and the drawings.

DETAILED DESCRIPTION OF THE INVENTION

Figure 3:
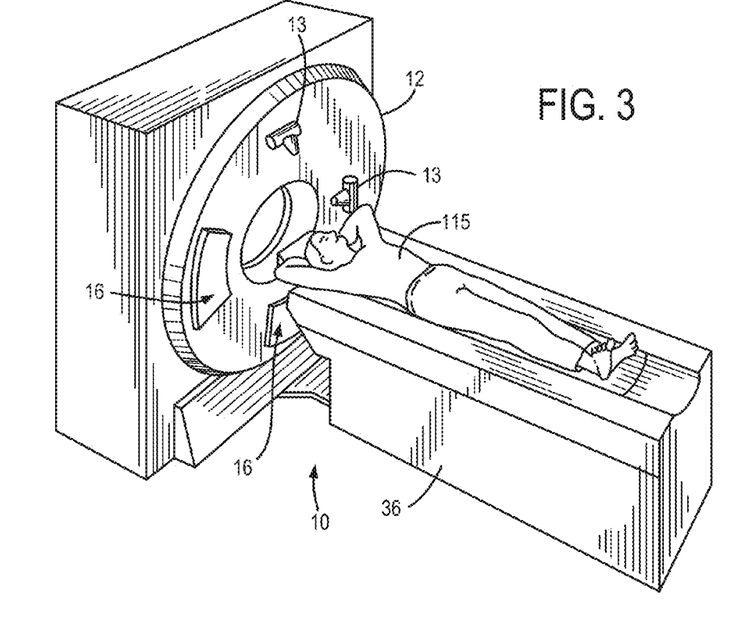
FIG. 3 is pictorial view of a CT imaging system in which the present invention may be employed.
Figure 4:
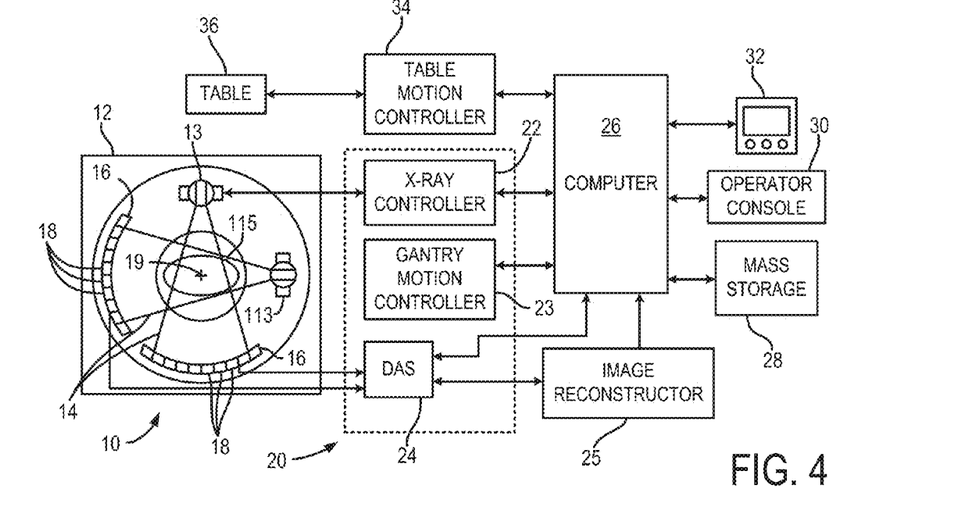
FIG. 4 is block schematic diagram of the CT imaging system of FIG. 3.

With initial reference to FIGS. 3 and 4, a computed tomography (CT) imaging system 10 includes a gantry 12 representative of at least a "third generation" CT scanner. In the illustrated example, the gantry 12 has a pair of x-ray sources 13 that each project a fan beam or cone beam of x-rays 14 toward a detector array 16 on the opposite side of the gantry 12. However, it is specifically noted that the present invention, while readily applicable to dual-source, dual-energy CT systems, is also readily applicable to other multi-energy CT systems and methods, such as single-source, dual- or multi-energy CT systems and methods. The detector array 16 is formed by a number of detector elements 18 that together sense the projected x-rays that pass through a medical patient 15. As will be described, it is contemplated that the detector array 16 may form part of a so-called "photon-counting" and/or "energy-discriminating" detector system. In any case, each detector element 18 produces an electrical signal that represents the intensity of an impinging x-ray beam or, more accurately, each photon or bunch of photons, and hence the attenuation of the beam (or photons) as it passes through the patient. During a scan to acquire x-ray projection data, the gantry 12 and the components mounted thereon rotate about a center of rotation 19 located within the patient 15 to acquire attenuation data.

The rotation of the gantry and the operation of the x-ray source(s) 13 are governed by a control mechanism 20 of the CT system. The control mechanism 20 includes an x-ray controller 22 that provides power and timing signals to the x-ray sources 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 28.

The computer 26 also receives commands and scanning parameters from an operator via console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22, and the gantry motor controller 23. In addition, computer 26 operates a table motor controller 34 that controls a motorized table 36 to position the patient 15 in the gantry 12.

In CT scans, image noise is highly correlated to the number of photons received. Thus, lower noise in a resulting image is achieved when more x-ray photons are used to create the image. For this reason, traditional notions of CT imaging focus including all usable x-ray information. However, spectral CT imaging diverts from this notion by segregating the information into bins. The present invention recognizes that spectral CT is, in essence, an imaging technique in four dimensions. In particular, spectral CT deals with the three dimensions in space and a unique dimension in energy. Within this conceptual context, the present invention recognizes that time-resolved spectral CT includes a $5^{th}$ dimension, namely a dimension of time.

The present invention builds on the above recognition that spectral CT is, in essence, an imaging technique in four dimensions (or five dimensions, in the case of a time series of images) and further recognizes that a high degree of correlation exists between the energy-specific data sets of spectral CT imaging due to the fact that the data sets pertain to the same patient anatomy. Using these recognitions, the present invention exploits this correlation of information in the energy domain to reduce image noise in each energy-specific image, not just in a processed material composition image. That is, although extensive research has been conducted in the spatial and temporal domains to reduce noise and improve image quality, generally, limited investigation has been done in energy domain. Currently, data acquired from each energy bin in the energy domain is treated independently and CT images at each energy utilize only data from a single energy bin. As will be described, the present invention diverts from this traditional notion and ultimately improves material differentiation in spectral CT by allowing selection of the optimal or desired energy bins and, in particular, the number of bins, the width of the bins, and the location of the bins, without paying a substantial noise penalty.

In x-ray CT, image noise is inversely related to the square root of the total number of photons used to reconstruct the image. The number of photons associated with each energy bin image in spectral CT is reduced for the same patient exposure because of dividing the total number of photons applied to the patient into multiple energy bins to obtain energy specific information. Noise level therefore increases compared to conventional CT images that use all available photons. The degree of noise increase depends on the number of energy bins and the width of each energy bin. By utilizing the redundant information in the energy domain, image noise in spectral CT can be reduced to the level of conventional CT.

Thus, the present invention recognizes that, in the case of multi-energy CT imaging, images reconstructed from all received photons can be treated as "conventional" CT images that have little or no material differentiating information (energy-resolved signal), but which also have the lowest noise and use the full dose applied to the patient. Comparing these "conventional" images reconstructed from all received photons and images reconstructed from each energy bin in a multi-energy acquisition illustrates that the images are not independent. Rather, the images actually have a high degree of correlation due to the fact that they measure the same anatomy. The present invention exploits this correlation to generate new energy-specific, CT image sets that have dramatically reduced noise levels, such as is generally achievable with conventional CT images, yet maintain the CT numbers of individual energy bin images. These images retain each individual data set's specific energy signature, while noise can be reduced to as low as that of the conventional image that is reconstructed directly from all acquired photons.

Figure 5:
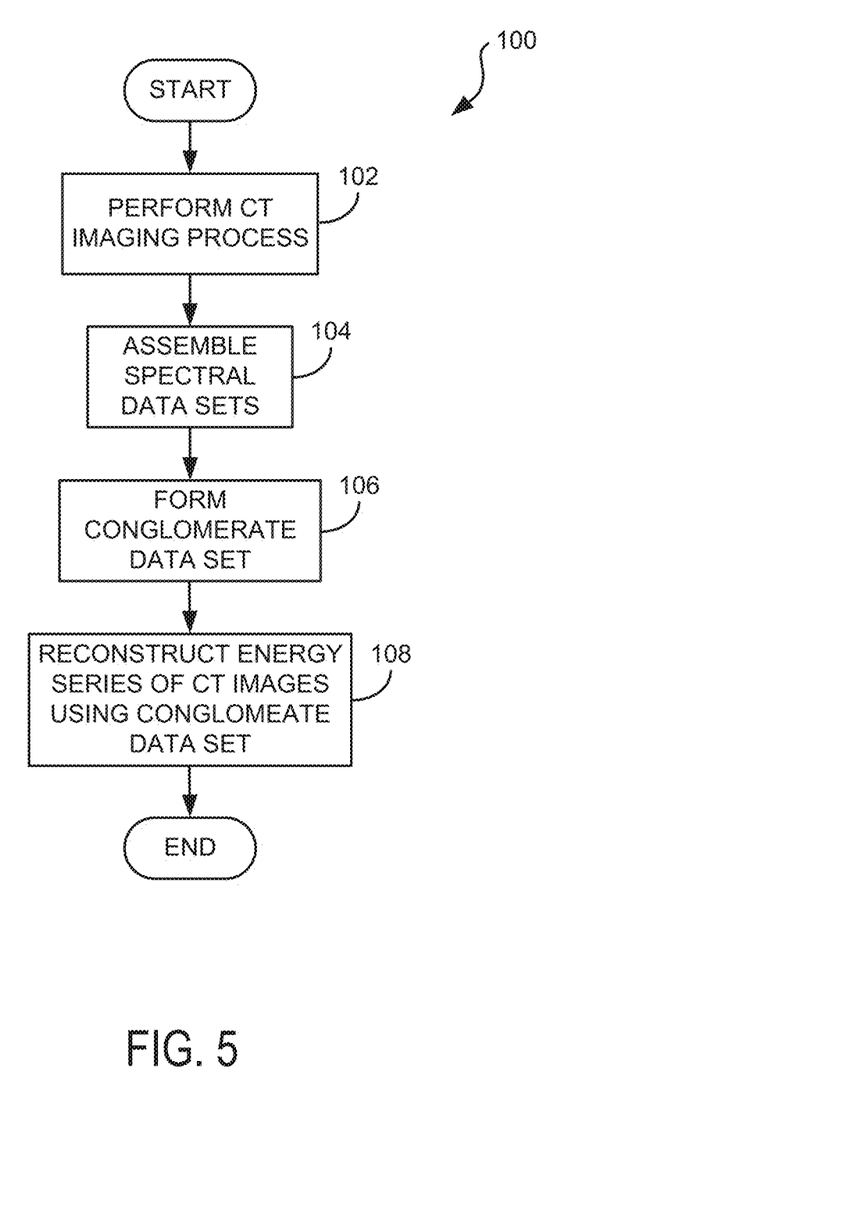
FIG. 5 is a flow chart setting forth exemplary steps of a method for creating an enhanced series of images in accordance with the present invention.

Turning now to FIG. 5, a process for imaging in accordance with the present invention will be described with respect to exemplary steps embodied as a flow chart 100. The process begins with the performance of a CT imaging process, at process block 102, such as using the above-described CT systems, including PC or ED CT systems. In this sense, it is contemplated that the CT imaging process may be a traditional "multi-energy" CT imaging process, including, for example, the common "dual-energy" and "dual-energy, dual-source" CT imaging processes. In addition, it is contemplated, for example, when using the aforementioned PC or ED CT systems, that the CT process may deviate from traditional "multi-energy" CT acquisitions, so long as the ability to discriminate and bin the acquired data based on energy is maintained. To this point, at process block 104, the acquired CT data is assembled or assigned, as described above, into bins that serve to divide the acquired CT data into spectral data sets.

As noted above, the present invention recognizes that these spectral data sets are, in essence, multi-dimensional data sets, where one of the dimensions spans the energy series. For example, if the acquired CT data is three dimensional (3D) in the sense of acquiring CT in three spatial dimensions, spectral data sets are treated as four dimensional (4D) data sets. Similarly, if the acquired CT data is two dimensional (2D) in the sense of acquiring CT data in two spatial dimensions or the acquired CT data is 3D in the sense of acquiring CT data in 3 spatial dimensions and across a time series, the spectral data sets represent 3D or 5D data sets, respectively, in the context of the present invention. The present invention further recognizes that a high degree of correlation exists between the spectral data sets due to the fact that the data sets pertain to the same patient anatomy. Using this information, the present invention, at process block 106, forms a "conglomerate data set" that includes data spanning the various spectral data sets assembled at process block 104. For example, data from bins associated with 20-40 keV, 40-60 keV, 60-80 keV, and the like can serve as the bins across which the conglomerate data set spans. Put another way, the conglomerate data set and, any conglomerate image, is formed from CT from a variety of different energy bins used to segregate the CT data acquired using the multi-energy imaging process at process block 102. As will be explained in detail, this conglomerate data set and/or any associated conglomerate image formed therefrom may be used to reconstruct an energy series of CT images at process block 108 that has substantially improved material differentiation achieved without a substantial noise penalty incurred using traditional methods.

In accordance with some implementations, the "conglomerate data set" or conglomerate image may use a substantial amount or even most or all x-ray photons received and associated with the energy bins. By using a conglomerate data set during the reconstruction of individual energy images from the data associated with each individual energy bin, the trade-off between bin number (or width) and image noise is substantially reduced or, for clinical purposes, effectively eliminated. This provides previously-unachievable flexibility to choose energy bins based upon signal optimization so that the best material identification/differentiation information can be achieved without the images succumbing to noise. Therefore, the constraints presented in FIGS. 1 and 2 can be managed in a clinical setting, without paying the significant penalty of either increased image noise or increased patient dose.

A variety of methods are contemplated for creating a conglomerate data set and reconstructing an energy series of images using the conglomerate data set or image. For example, two methods include a HighlY constrained back-PRojection (HYPR) processing and reconstruction and a Prior Image Constrained Compressed Sensing (PICCS), Non-convex PICCS, and multi-band filtration. Exemplary HYPR and HYPR-based methods are described in U.S. Pat. No. 7,519,412, which is incorporated herein by reference. Exemplary PICCS and PICCS-based methods are described in US Patent Application Publication No. 2009/0161932, which is incorporated herein by reference.

In accordance with one aspect of the invention, the "conglomerate image" may be provided by applying the concepts creating a "composite image" as described within the context of HYPR, to use the acquired photon data that spans multiple energy bins to form the conglomerate data set. HYPR and its modified version, HYPR-LR, allow the reconstruction of a time or other series images from highly undersampled data set using a "composite image" built from multiple time series of images. HYPR-LR and HYPR-LR-related methods are described in U.S. Patent Publication No. 2008-0219535, which is incorporated herein by reference. These HYPR-based concepts, which were first applied to a time series of images, can be used in accordance with the present invention to reconstruct an energy series of images formed of separate images, as will be described.

It has been demonstrated that the signal to noise ratio (SNR) of HYPR-reconstructed images are determined by the composite image instead of the single frame image, which improves the SNR of images at each time frame. The HYPR technique and general concepts thereof can be adapted into spectral CT imaging to provide a "conglomerate data set" or "conglomerate image" to improve SNR of images at each individual energy bin. In this regard, the "composite image" of HYPR and the concepts for creation of the "composite image" may be extended to the above-described energy series to form a "conglomerate data set" or "conglomerate image" in the context of the present invention.

A "conglomerate data set" or "conglomerate image" in the context of the present invention may be formed using the concept of a "composite image" in HYPR by using x-ray photons acquired across the energy spectrum and respective bins and, thereby, a "composite data set" or "conglomerate data set" can be formed having the SNR that is independent of the number of energy bins. That is, as the SNR of HYPR images is determined by the composite image, in the present invention, images at each energy bin therefore have an SNR equivalent to that obtained with all x-ray photons. For example, these conglomerate images can be generated using an averaging or may be generated by applying different weighting factors to each energy bin, which may improve image quality. By reconstructing the individual energy images associated with each energy bin using a conglomerate image and a HYPR-based reconstruction, the tradeoff between number of energy bins and image noise in each energy bin is substantially reduced or eliminated.

Figure 6:
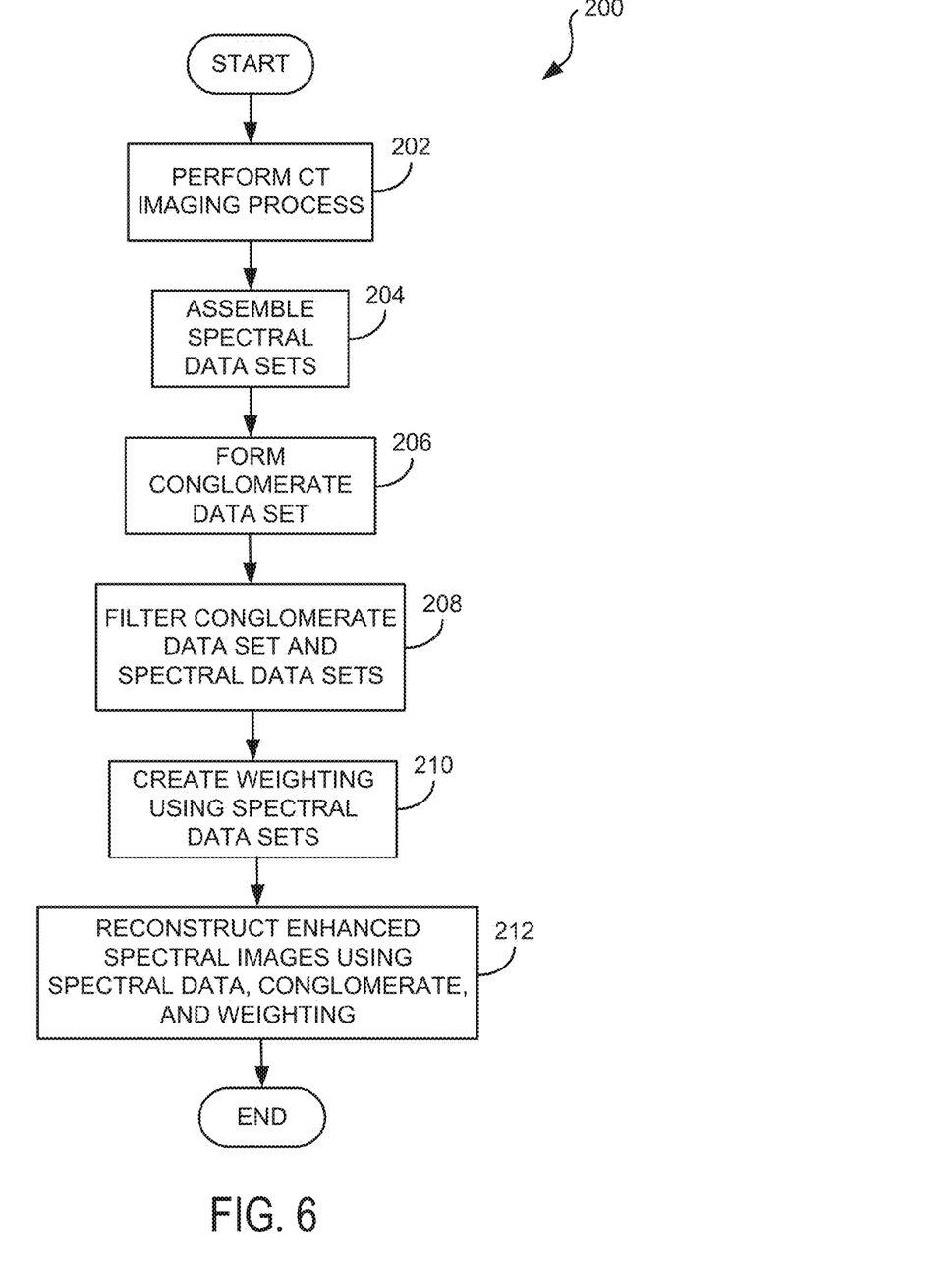
FIG. 6 is a flow chart setting forth exemplary steps of a method utilizing HYPR-based techniques to create an enhanced series of images in accordance with the present invention.

Turning to FIG. 6, a specific example, using the HYPR-LR concept of a "composite image" and reconstruction, is provided by way of a flow chart 200. The exemplary process using HYPR-based techniques begins by performing a CT imaging process. As explained above, it is contemplated that the CT imaging process may be a traditional "multi-energy" CT imaging process, including, for example, the common "dual-energy" and "dual-energy, dual-source" CT imaging processes. In addition, it is contemplated, for example, when using the aforementioned PC or ED CT systems, that the CT process may deviate from traditional "multi-energy" CT acquisitions, so long as the ability to discriminate and bin the acquired data based on energy is maintained. To this point, at process block 204, the acquired CT data is assembled or assigned, as described above, into bins that serve to divide the acquired CT data into spectral data sets.

As previously described with respect to FIG. 5, a conglomerate data set is then formed from the spectral data sets at process block 206. However, within this example utilizing HYPR-based techniques for forming the conglomerate data set and reconstructing the energy series of images, a conglomerate image $I_C$ may be produced by averaging data from some or all of the energy bins. In some cases, all of the data from all of the bins may be used to ensure that all available photons are included in the conglomerate image to, thereby, produce the lowest image noise. At process block 208 a filter operation is then performed on both individual energy data sets or images $I_E$ and the composite data set/image $I_C$. At process block 210, a weighting or weighting image is obtained as the ratio between individual energy data sets or images $I_E$ and the composite data set/image $I_C$, as filtered. At process block 212, HYPR "processing" or reconstruction, for example, HYPR-LR processing, can then be used to form an enhanced spectral image $I_{HE}$ as the multiplication of the weighting image and the conglomerate image. Mathematically, the HYPR-LR algorithm can be expressed as:

$$I_{HE} = \frac{I_E \otimes K}{I_C \otimes K} \cdot I_C; \qquad \text{Eqn. 1}$$

where K is a low-pass filter kernel. A kernel, such as a 7×7 pixel uniform square kernel or other desirable kernel, can be used. The symbol "$\otimes$" represents a convolution process.

Using error propagation theory, image noise after such HYPR-LR processing has been derived in MRI images and CT images. It can be expressed as:

$$\sigma^2_{I_{HE}} \approx \sigma^2_{I_C} + \frac{\sigma^2_{I_E}}{N_K} + \frac{2\sigma^2_{I_C}}{N_K};\qquad\text{Eqn. 2}$$

where $\sigma_{I_{HE}}^2$ is the noise variance in the HYPR-LR processed images at energy bin E, $\sigma_{I_C}^2$ is the noise variance in composite image, $\sigma_{I_E}^2$ is the noise variance in individual energy bin image, and $N_K$ is the number of pixels used in the filter kernel. It can be observed that the noise variance of HYPR-LR images is mainly determined by that of the composite images and this translates to the present invention and the use of HYPR-LR with a "conglomerate image." Thus, in the present invention, noise variance is mainly determined by that of the composite images and only weakly depends on that of individual energy bin image. This relationship is more obvious if the energy bins are selected in such a way that similar noise is measured in each individual energy bin $$(\sigma^2_{I_E} = N_E \times \sigma^2_{I_C}).$$

In this scenario, Eqn. 2 can be rewritten as:

$$\sigma^2_{I_{HE}} \approx \sigma^2_{I_C}\left(1 + \frac{N_E + 2}{N_K}\right);\qquad\text{Eqn. 3}$$

where $N_E$ is the number of energy bins. In practice, $N_E$ (number of energy bins) is usually much smaller than $N_K$ due to physical limitations in the detector hardware. Therefore, the noise variance of images $\sigma_{I_{HE}}^2$ in the enhanced energy series is expected to be close to that of conglomerate image.

It is noted that the size of the convolution kernel used for the HYPR-LR processing has an impact on CT number accuracy and image noise reduction. As seen from Eqns. (2) and (3), image noise is reduced as kernel size increases, although the incremental noise reduction diminishes as the noise level approaches the noise level of composite image. A very large kernel could affect CT number accuracy and consequently energy specific information. A 7×7 pixel uniform filter kernel has been demonstrated as a reasonable choice to reduce image noise without affecting CT number accuracy or spatial resolution. One limitation of the HYPR-LR algorithm is that it prefers imaging scenarios without substantial motion between energy-specific images. However, in most spectral CT systems (e.g. photon-counting, detector-based or dual-source CT systems), imaging data at different beam energies are acquired simultaneously. Therefore, motion is of minimal concern. For systems in which substantial delay is expected between different energy data acquisitions (e.g. dual energy CT using two separate scans), motion might be a concern and HYPR-LR techniques should be adjusted to account for motion.

Figure 7A:
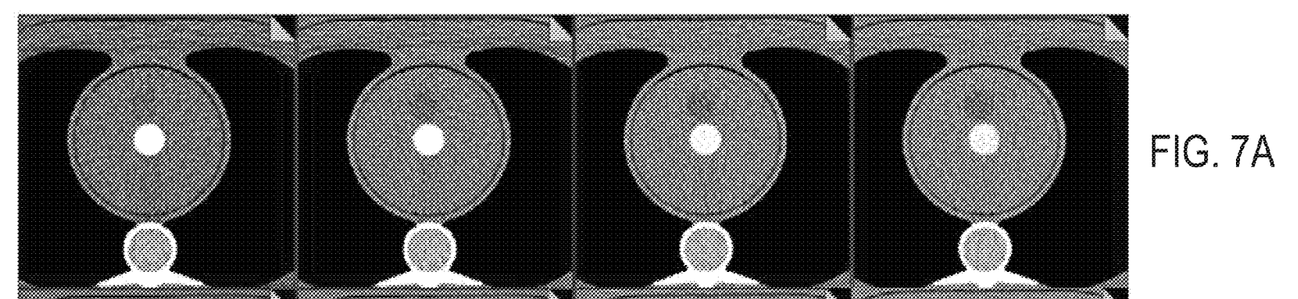
FIG. 7A is a series of images reconstructed without the use of a conglomerate image spanning all energy bins.
Figure 7B:
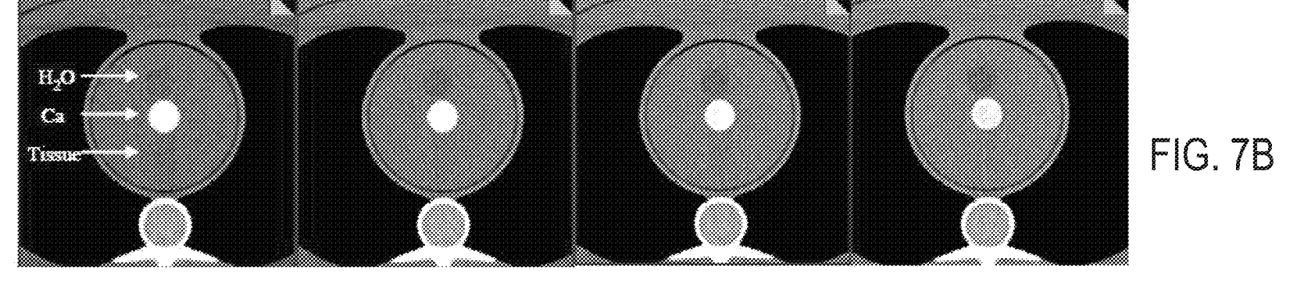
FIG. 7B is a series of images reconstructed using HYPR-LR to provide a conglomerate image spanning all energy bins and, thereafter, reconstruct a series of energy images at 80, 100, 120, and 140 kVp.

To demonstrate this effect, CT numbers and noise variances can be measured inside three circular ROIs placed at regions representing calcium, water, and soft tissue. The measurement can be conducted on images reconstructed using both commercial software and HYPR-LR for comparison. Noise reduction using HYPR-LR is then calculated, and corresponding dose reduction is estimated based upon the relationship between radiation dose and image noise. Images of a semi-anthropomorphic thoracic phantom scanned at 80, 100, 120, and 140 kVp are shown in FIGS. 7A and 7B. Specifically, FIG. 7A shows images reconstructed without the aid of the present invention and FIG. 7B shows images processed with the present invention and HYPR providing the composite image as the conglomerate image. Significant noise reduction was observed after HYPR processing for images at each beam energy. Due to the high image noise in the original image, the water-equivalent rod, which is labeled in FIG. 7B, is almost not differentiable in the images of FIG. 7A. On the other hand, in the images of FIG. 7B, the water-equivalent rod is clearly seen. This distinction between the images of FIGS. 7A and 7B is due to the use of a conglomerate image that reduces noise and increases SNR in the resulting images.

Thus, HYPR-LR processing applied in the context of the present invention did not alter spatial resolution or energy-specific CT numbers. The effectiveness of the present invention readily translates to both photon-counting, detector-based and integrating, detector-based CT systems using numerical simulations, phantom, and patient studies. Numerical simulations demonstrated a 36-76% noise reduction using the present invention with HYPR-LR processing in the energy domain compared to standard FBP reconstruction for the case when 6 energy bins were used. The percent noise reduction changed when different numbers of energy bins or different bin widths were used.

Figure 8:
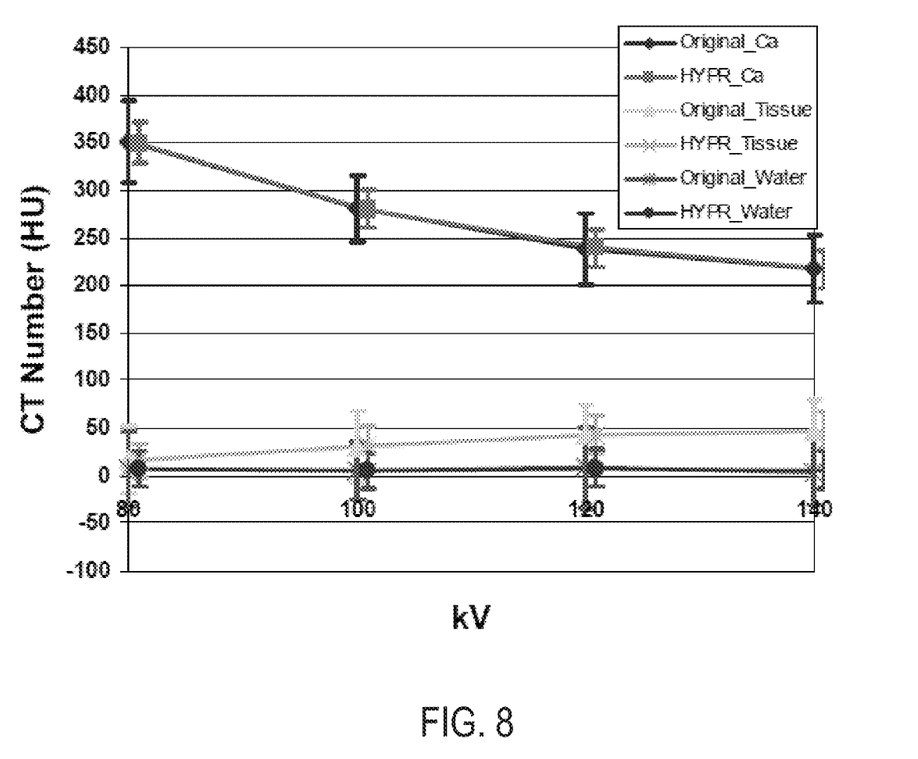
FIG. 8 is a graph showing CT number and noise measured at ROIs representing calcium, water, and soft tissue across a number of reconstruction methods.

Turing now to FIG. 8, the CT number (as mean) and image noise (as standard variation) of calcium, water, and tissue equivalent are shown. The energy dependent CT numbers for different materials makes it possible for material differentiation using spectral CT. The same CT numbers were maintained after applying the present invention compared with the original CT numbers. Noise reduction using the present invention can be observed by the smaller error bars compared with those in original images. The percentage of noise reduction is shown in Table I.

TABLE I

| | Percent noise reduction | | | |
|---|---|---|---|---|
| kVp | Ca | Water | Tissue | Average |
| 80 | 50% | 51% | 51% | 51% |
| 100 | 43% | 37% | 44% | 41% |
| 120 | 49% | 53% | 37% | 46% |
| 140 | 45% | 45% | 44% | 45% |

Overall, an approximately 50 percent noise reduction is achieved using a conglomerate image and HYPR-based reconstruction. Based upon the relationship between noise and radiation dose (Dose~1/noise^2), this is equivalent to a factor of 4 dose reduction given the same image noise. These results could be interpreted as noise reduction given the same radiation dose, dose reduction given the same image noise, or the combination of these two.

CT numbers were well preserved using the present invention and image noise was comparable to that of the composite image using all photons, significantly reduced compared with standard filter backprojection (FBP) algorithms. This breaks the trade-off between image noise and energy bin size and/or numbers, which allows flexibility to use optimal energy bins for best spectral imaging.

Radiation dose reduction can be achieved with the reduced image noise using the present invention. As addressed above, other processing techniques for forming the conglomerate data set and reconstructing the energy series of images are contemplated, including Prior Image Constrained Compressed Sensing (PICCS) image reconstruction. In this case, the conglomerate image may serve as the so-called "prior image" of PICCS in PICCS-based reconstruction.

As a simple special case, dual-energy CT, which is now clinically used for stone composition differentiation, bone removal in CT angiography, gout detection, and iodine quantitifcation, can also benefit from this approach. In current clinical dual-energy CT implementations, x-ray photons are approximately equally distributed into the low and high energy scans. Each image set then uses only one half of the total radiation dose delivered to the patient and has higher noise compared with a conventional (single energy) CT that uses the full dose to the patient. The method of the present invention improves the noise property of each image set to that of the conventional (single energy) full dose images, while preserving energy-selective information for dual energy processing.

Thus, dual-energy CT, which is one specific implementation of the more general spectral CT, has been shown to provide clinically useful diagnostic information beyond what is available with conventional single energy CT. Using the present invention, noise can be reduced in both the low- and high-energy images of a dual energy CT exam. For example, HYPR-LR processing may be conducted in low- and high-energy images before material decomposition. Noise can also reduced after material-specific processing is performed to subtract iodine signal (i.e. to create a virtual, non-contrast-enhanced dataset). Because noise is reduced in both the low- and high-energy images, any other dual energy processing algorithms, such as those performed to simulate monoenergetic images, also benefit from this invention. Furthermore, it is contemplated that the above-described methods may be used to process image data after material decomposition has been performed. In such case, a "enhanced" material-specific image may be generated in accordance with the above-described processes.

In CT imaging, image noise is inversely proportional to the number of available photons. Therefore, image noise in spectral CT for each individual energy bin is determined by the number of photons falling inside the energy range. The tradeoff between using more energy bins (providing more energy specific measurements) and decreasing image noise (providing more photons) has to be considered. Noise is primarily determined by the conglomerate image, which may use all the applied photons instead of only the photons falling within a single energy bin. This has been demonstrated using 2, 4, and 6 energy bins with a dual energy CT patient exam (2 bins), conventional CT phantom scans (4 bins), photon-counting μ-CT (6 bins) and numerical simulations (6 bins). More (greater than 2) energy bins could be used without substantially increasing image noise. However, the number of energy bins cannot be increased arbitrarily for a number of reasons. First, the maximal number of energy bins is mainly determined by the detector hardware. Second, based on Eqns. (2) and (3), increasing the number of bins will slightly increase image noise, especially when the number of bins becomes comparable to the number of pixels in the convolution kernel. Third, the incremental benefit of increasing the number of energy bins might not be significant once it reaches a certain level. Currently, many photon counting detectors operate using 2-8 energy bins. In this range, the increase in image noise using more energy bins is negligible after processing, and the tradeoff between more energy bins (more energy specific information) and more photons (less noise) is practically avoided.

In conclusion, it has been demonstrated the ability to substantially reduce noise in spectral CT images by exploiting information redundancies in the energy domain. The ability to reduce image noise to the level of a conventional CT image that uses all available photons eliminates the need to trade off image noise (and hence, patient dose) and the number and width of energy bins. This approach provides maximal flexibility for energy beam optimization without paying a price in terms of increased noise or dose.

The present invention has been described in accordance with the embodiments shown, and one of ordinary skill in the art will readily recognize that there could be variations to the embodiments, and any variations would be within the spirit and scope of the present invention. Accordingly, many modifications may be made by one of ordinary skill in the art without departing from the spirit and scope of the appended claims.

The invention claimed is:

1. A method for producing enhanced computed tomography (CT) images, the method comprising the steps of:
   (a) acquiring a series of energy data sets, each energy data set associated with at least one energy bin of an energy spectrum;
   (b) reconstructing, using a computer system, a series of energy images using the series of energy data sets;
   (c) generating, using the computer system, a conglomerate image using a combination of the series of energy images; and
   (d) generating, using the conglomerate image, the time series of energy images and a model, at least one of an enhanced image and an enhanced material-specific image, wherein the model is configured such that a noise variance of the at least one of the enhanced image and the enhanced material-specific image is substantially determined by the conglomerate image.

2. The method of claim 1, wherein the method further comprises generating the conglomerate image using an average of the series of energy images.

3. The method of claim 1, wherein the method further comprises normalizing one or more images in the time series of energy images using information derived from the conglomerate image and multiplying the normalized result with the conglomerate image.

4. The method of claim 1, wherein the at least one of the enhanced image and the enhanced material-specific image is a monoenergetic image.

5. The method of claim 1, wherein the method further comprises generating the conglomerate image using a weighted sum of the series of energy images.

6. The method of claim 1, wherein the method further comprises performing a filter operation on one or more image of the series of energy images and the conglomerate image.

7. The method of claim 6 wherein the filter operation comprises applying a uniform filter kernel in a convolution process.

8. The method of claim 7, wherein the uniform filter kernel is a low-pass filter kernel.

9. The method of claim 1, wherein the method further comprises applying a multi-band filtration to the series of energy images and using the filtered images to generate the conglomerate image.

10. The method of claim 9 wherein the method further comprises using the filtered energy images and the conglomerate image to generate the at least one of the enhanced image and the enhanced material-specific image.

11. A computed tomography (CT) imaging system comprising:
   an x-ray source configured to emit x-rays toward an object to be imaged;
   a detector configured to receive x-rays that are attenuated by the object;
   a data acquisition system (DAS) connected to the detector to receive an indication of received x-rays;
   a computer system coupled to the DAS to receive the indication of the received x-rays and programmed to:
      separate the indication of the received x-rays into a series of energy data sets based on an energy level associated with received x-rays;
      reconstruct a series of energy images using the series of energy data sets;
      produce a conglomerate image using a combination of the series of energy images; and
      generate at least one enhanced energy image using a model correlating the at least one enhanced energy with the conglomerate image and the series of energy images, wherein the model is configured such that a noise variance of the at least one enhanced energy image is substantially determined by the conglomerate image.

12. The CT imaging system of claim 11, wherein the detector includes at least one of a photon counting and energy discriminating CT detector.

13. The CT imaging system of claim 11, wherein the computer system is further programmed to compute a weighted sum of the series of energy images to generate the conglomerate image.

14. The CT imaging system of claim 11, wherein the computer system is further programmed to perform a filter operation on at least one of the series of energy images and the conglomerate image.

15. The CT imaging system of claim 11, wherein the filter operation comprises applying a multi-band filtration to the series of energy images and using the filtered images to generate the conglomerate image.

16. The CT imaging system of claim 11, wherein the computer system is further programmed to perform a HYPR-LR-based processing mathematically expressed as:

$$I_{HE} = \frac{I_E \otimes K}{I_C \otimes K} \cdot I_C;$$

where $I_{HE}$ represents an enhanced image in the at least one enhanced energy image, $I_E$ represents an image in the series of energy images, $I_C$ represents the conglomerate image, K represents a filter kernel, and $\otimes$ represents a convolution process.

17. The CT imaging system of claim 16 wherein the filter kernel is a low-pass filter kernel.

18. The CT imaging system of claim 11, wherein the computer system is further programmed to generate at least one enhanced material-specific image using the at least one enhanced energy image.

19. The CT imaging system of claim 11, wherein the at least one enhanced energy image is a monoenergetic image.

20. A method for producing enhanced computed tomography (CT) images, the method comprising the steps of:
   (a) acquiring a series of energy-selective data sets, each energy-selective data set being associated with at least a portion of an energy spectrum;
   (b) producing a conglomerate data set using a combination of the series of energy-selective data sets;
   (c) reconstructing a conglomerate image using a conglomerate data set; and
   (d) generating, using the conglomerate image and a model, at least one enhanced energy image, each image associated with at least one of the energy-selective data set, wherein the model is configured such that the at least one enhanced energy image has a noise variance substantially determined by the conglomerate image.

* * * * *